US00PP10895P

United States Patent [19]

Van Es

[11] Patent Number: Plant 10,895

[45] Date of Patent: May 11, 1999

[54] SPATHIPHYLLUM PLANT NAMED 'VANESSA'

[75] Inventor: Wim Van Es, Breda, Netherlands

[73] Assignee: Milestone Agriculture, Inc., Apopka, Fla.

[21] Appl. No.: 09/007,035

[22] Filed: Jan. 14, 1998

[51] Int. Cl.[6] ..... A01H 5/00

[52] U.S. Cl. ..... Plt./364

[58] Field of Search ..... Plt./364

*Primary Examiner*—Howard J. Locker
*Assistant Examiner*—Kent L. Bell
*Attorney, Agent, or Firm*—C. A. Whealy

[57] ABSTRACT

A distinct cultivar of Spathiphyllum plant named 'Vanessa', characterized by its upright and tall plant habit; rapid growth rate; large and numerous shiny dark green leaves that are held horizontal to the petiole; early flowering; numerous large white spathes that are positioned just above the foliage on strong and erect peduncles; and long-lasting spathes.

1 Drawing Sheet

The present invention relates to a new and distinct cultivar of Spathiphyllum plant, botanically known as Spathiphyllum, and hereinafter referred to by the cultivar name 'Vanessa'.

The new cultivar is a product of a planned and controlled breeding program conducted by the inventor in Breda, The Netherlands. The objective of the breeding program is to create new Spathiphyllum cultivars with full and dense plant form, dark green leaves and large flowers. The new cultivar originated from a deliberate cross by the inventor in 1991 between the nonpatented Spathiphyllum cultivar 'Euro-Gigant' as the female or seed parent and the nonpatented Spathiphyllum cultivar 'Mona Loa' as the male or pollen parent. The cultivar 'Vanessa' was discovered and selected by the inventor as a plant within the progeny of the stated cross in a controlled environment in Breda, The Netherlands.

In side-by-side comparisons conducted in Breda, The Netherlands, plants of the new Spathiphyllum differed from plants of the female parent, the cultivar 'Euro-Gigant', in the following characteristics:

1. Plants of the new Spathiphyllum have darker and narrower leaves than plants of the cultivar 'Euro-Gigant'.
2. Plants of the new Spathiphyllum have thicker stems than plants of the cultivar 'Euro-Gigant'.
3. Plants of the new Spathiphyllum have larger spathes than plants of the cultivar 'Euro-Gigant'.
4. Plants of the new Spathiphyllum are more floriferous than plants of the cultivar 'Euro-Gigant'.

In side-by-side comparisons conducted in Breda, The Netherlands, plants of the new Spathiphyllum differed from plants of the male parent, the cultivar 'Mona Loa', in the following characteristics:

1. Plants of the new Spathiphyllum have darker, narrower and more upright leaves than plants of the cultivar 'Mona Loa'.
2. Plants of the new Spathiphyllum have thicker stems than plants of the cultivar 'Mona Loa'.
3. Plants of the new Spathiphyllum are fuller and denser than plants of the cultivar 'Mona Loa'.
4. Plants of the new Spathiphyllum have larger spathes than plants of the cultivar 'Mona Loa'.

Asexual propagation of the new cultivar by division and/or tissue culture at Breda, The Netherlands, has shown that the unique features of this new Spathiphyllum plant are stable and reproduced true to type in successive generations of asexual propagation.

The new Spathiphyllum has not been observed under all possible environmental conditions. The phenotype may vary somewhat with variations in environment such as temperature and light intensity, without, however, any variance in genotype. The following observations, measurements and comparisons describe plants grown in Apopka, Fla., under commercial greenhouse conditions.

The following traits have been repeatedly observed and are determined to be the unique characteristics of 'Vanessa'. These characteristics in combination distinguish 'Vanessa' as a new and distinct cultivar:

1. Upright and tall plant habit.
2. Rapid growth rate.
3. Large and numerous shiny dark green leaves that are held horizontal to the petiole.
4. Early flowering.
5. Numerous large white spathes that are positioned just above the foliage on strong and erect peduncles.
6. Long-lasting spathes.

BRIEF DESCRIPTION OF THE PHOTOGRAPH

The accompanying colored photograph illustrates the overall appearance of the new cultivar, showing the colors as true as it is reasonably possible to obtain in colored reproductions of this type. The photograph comprises a side perspective view of a typical potted plant of 'Vanessa'.

DETAILED BOTANICAL DESCRIPTION

In the following description, color references are made to The Royal Horticultural Society Colour Chart except where general terms of ordinary dictionary significance are used.

Botanical classification: Spathiphyllum cultivar 'Vanessa'.

Parentage:

*Female parent.*—Spathiphyllum cultivar 'Euro-Gigant', not patented.

*Male parent.*—Spathiphyllum cultivar 'Mona Loa', not patented.

Propagation:

*Type.*—By division or by tissue culture.

*Time to initiate roots.*—Winter: About 12 days at 20° C. Summer: About 7 days at 26° C.

*Rooting habit.*—Freely branching, numerous fleshy roots.

Plant description:

*Plant shape.*—Upright, inverted triangle, symmetrical.

*Growth habit.*—Erect when young, becoming outwardly arching as leaves develop. Numerous side shoots give plants a full, dense appearance. Large plant size, appropriate for 25-cm and larger containers.

*Plant height.*—About 62 cm from soil level to top of leaf plane.

*Plant vigor.*—Vigorous, rapid growth rate.

*Foliage description.*—Leaf shape: Lanceolate. Leaf length: About 38 cm. Leaf width: About 16 cm. Margin: Entire. Leaf surface: Flat, rugose, shiny. Leaf tip: Tapered, acuminate. Leaf base: Obtuse. Leaf aspect: Young leaves upright, mature leaves held perpendicular to petiole. Leaf texture: Leathery, smooth, glabrous, durable. Leaf color: Young, top side: Darker than 137A. Young, under side: Close to 137C. Mature, top side: Darker than 147A. Mature, under side: Lighter than 147A. Venation: Top side, midvein: Close to 137B, sunken. Under side: Close to 144C, prominent. Petiole length, primary shoots: About 45 cm. Petiole diameter, primary shoots, just below geniculum: About 6 mm. Geniculum diameter, primary shoots: About 7 mm. Petiole wing, primary shoots: Apparent on lower two thirds of mature leaf petiole. Petiole color: Young: 144A. Fully developed: Winged area: 147A. Above winged area: 147A. Geniculum: 144A.

Inflorescence description:

*Inflorescence arrangement.*—Large concave spathe with spadix held about 15 cm above the foliage. Numerous inflorescences arise from leaf axils.

*Spathe longevity.*—Spathes are long-lasting, generally maintaining white color for about 8 weeks on the plant depending on light and temperature levels.

*Spathe.*—Shape: Ovate. Size: Length: About 13 cm. Width: About 8 cm. Aspect: Concave, curving over the spadix. Color: Before unrolling: White, 155D/155A. Open spathe: White, 155D/155A, with green, 146A, adaxial midvein.

*Spadix.*—Size: Length: About 7.5 cm. Diameter: About 1.5 cm. Color: White. Pollen: White, abundant.

*Peduncle.*—Aspect: Strong and erect. Size: Length: About 65 cm. Diameter: About 6 mm. Color: 147A.

Disease resistance: No known Spathiphyllum diseases observed to date on plants grown under commercial greenhouse conditions.

Seed development: Seed development has not been observed.

It is claimed:

1. A new and distinct cultivar of Spathiphyllum plant named 'Vanessa', as illustrated and described.

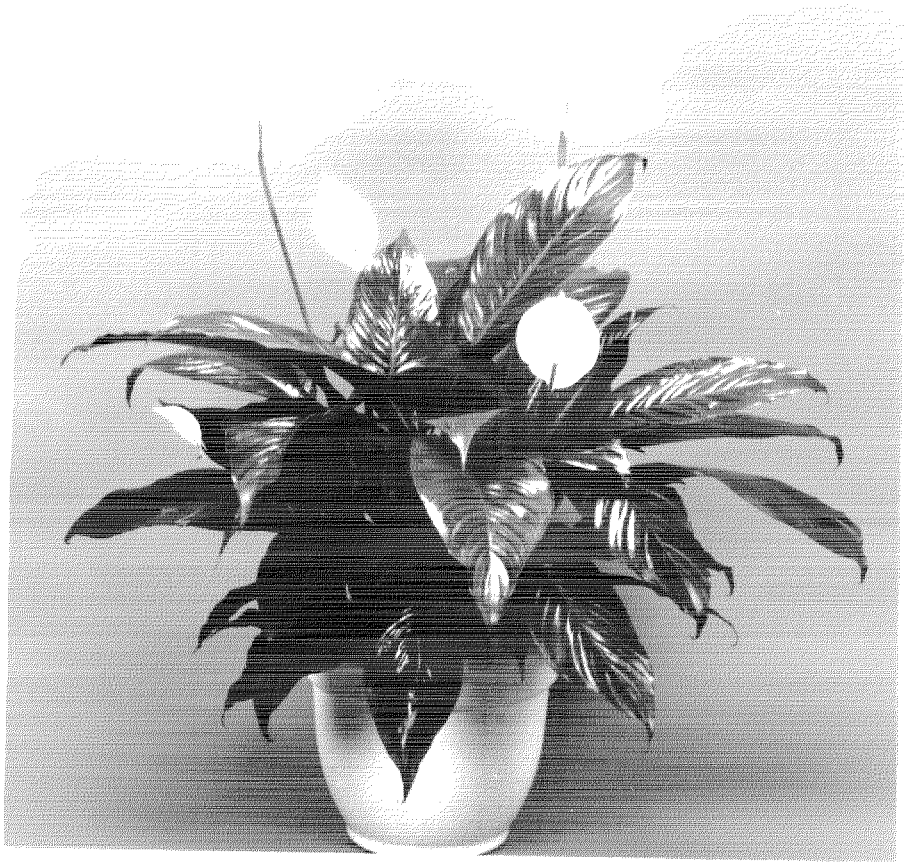

* * * * *